United States Patent [19]

Tararuj et al.

[11] Patent Number: 4,952,400
[45] Date of Patent: Aug. 28, 1990

[54] POWDER AND MICROCAPSULE FRAGRANCE ENHANCED SAMPLER

[75] Inventors: Christopher Tararuj, Mercerville; Carl K. Schaab, Princeton Jct., both of N.J.

[73] Assignee: Webcraft Technologies, Inc., North Brunswick, N.J.

[21] Appl. No.: 207,804

[22] Filed: Jun. 17, 1988

[51] Int. Cl.$^5$ ............................ B32B 5/30; B32B 5/16
[52] U.S. Cl. ................................... 424/401; 434/377; 428/321.5; 428/905; 428/402.2
[58] Field of Search ............... 434/377; 428/402.2, 428/905, 321.5; 424/401

[56] References Cited

U.S. PATENT DOCUMENTS

| | | | |
|---|---|---|---|
| 4,446,032 | 0/1984 | Munteanu et al. | 428/905 |
| 4,661,388 | 4/1987 | Charbonneau | 428/402.2 |
| 4,681,806 | 7/1987 | Matkan et al. | 428/402.21 |
| 4,752,496 | 6/1988 | Fellows | 427/27 |

Primary Examiner—Edward M. Coven
Assistant Examiner—Valerie Szczepanik
Attorney, Agent, or Firm—Shlesinger & Myers

[57] ABSTRACT

A cosmetic sampler has a thin dry layer of powder particles which are fragrance enhanced by fragrance containing microcapsules. The fragrance powder and microcapsules are applied as a production state, in a mass produced printed sampler manufacturing process from a liquid slurry which dries rapidly. The individual powder particles on the finished sampler item are raedily removed from the web surface by light finger pressure as a free flowing powder and the microcapsules are simultaneously ruptured to produce the desired fragrance.

6 Claims, 3 Drawing Sheets

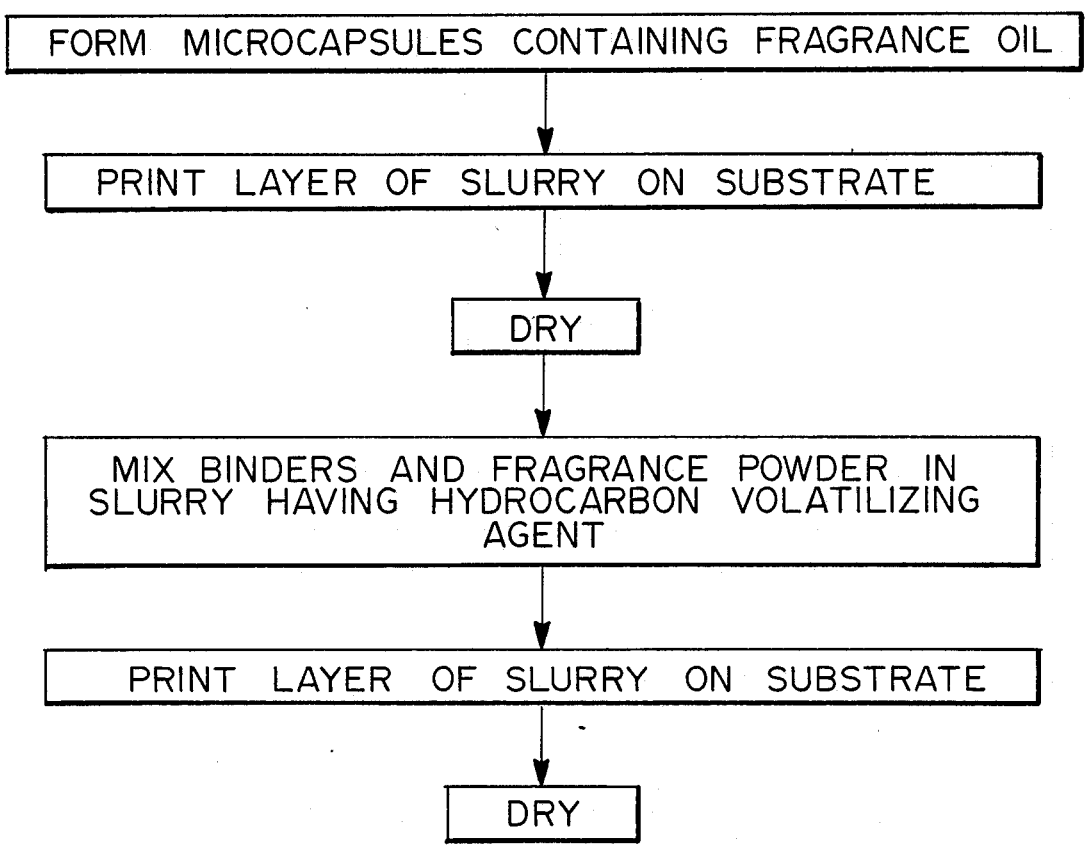
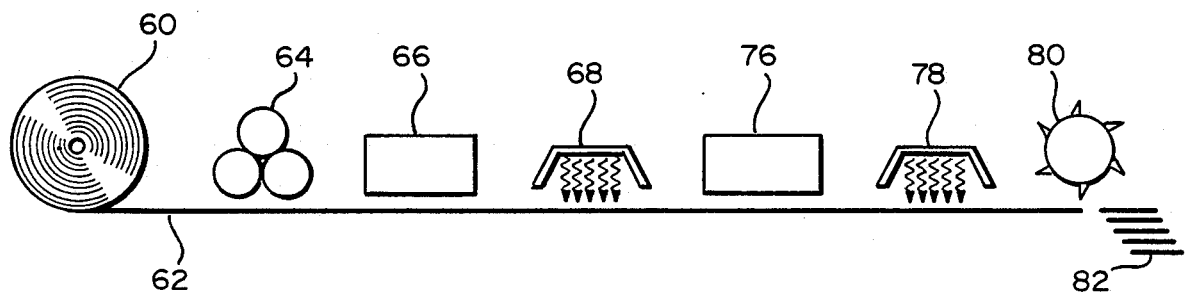

POWDER AND MICROCAPSULE FRAGRANCE ENHANCED SAMPLER

BACKGROUND OF THE INVENTION

This invention relates to mass distributed sample strip items, and particularly to a cosmetic type sampler piece which has a representative fragranced powder sample.

The recent introduction of mass distributed paper sample pieces as an advertising item, having a sample of the product advertised, as met with general acceptance and usage for perfumes, cosmetic blushes, and lipsticks. Such samplers, either distributed through advertising inserts, or by mass newspaper and mailing distributions, have proved to be effective advertising items.

All of the products on these samplers have a physical coherence which permits them to readily be placed on a substrate to which they will adhere without degradation, such as flaking, during handling and distribution.

It has not been possible to do this with powder items in the cosmetic line, for example, because they are particulate. The requirements of a dry free flowing particulate sample on removal present a problem with respect to adherence of the product to the sampler item during distribution and handling.

SUMMARY OF THE INVENTION

Accordingly, it is a principal feature of this invention to provide a sampler piece which can carry particulate powder layers in a dry state, which will not disintegrate during handling and shipping, and are removable from the sampler as a free flowing discrete particle powder by light finger pressure of the sampler recipient.

It is another feature of this invention to provide a representative sample powder which has an enhanced fragrance at the time of removal indicative of the fragrance of a freshly opened package of the product represented.

It is a further feature of this invention to provide an effective low cost sampler piece for advertising purposes having substantially greater message impact because of the inclusion of the powder sample.

It is a further object of this invention to provide a method for producing a powder advertising sampler.

It is a general feature of this invention to provide a combination of fragrance and powder which can be coated on a sampler to advertise cosmetic and talc powders.

It is a further feature of this invention to provide a cosmetic sampler having a readily removable fragranced powder, and which has a relatively long shelf life due to sealing of fragrance scent oils within the sampler layer and its constituents.

It is still a further feature of this invention to provide a fragrance enhancing capability to the particles particles in the layer.

It is another feature of this invention to provide an effective low cost sampler piece which can be used by advertisers through large scale distribution channels.

It is a further feature of this invention to provide a readily appliable liquid composition, containing powder and fragrance constituents, which can be applied by mass production techniques to a substrate, such as a printed paper web, which will on drying harden to a sufficiently durable cohesive strip to permit handling and distribution.

These and other features and advantages of the invention will become apparent from the following description and claims.

DESCRIPTION OF THE DRAWINGS

FIG. 7 shows the steps of preparing and applying the particle and microcapsule layers to the sampler of FIG. 5.

FIG. 8 schematically shows the production steps for producing the sampler of FIG. 5.

DESCRIPTION OF THE INVENTION

Figure 1:
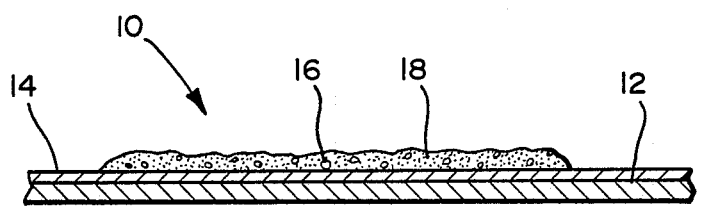
FIG. 1 is a cross-sectional view of a cosmetic sampler through the fragrance powder layer section thereof.

The cosmetic sampler that is shown in FIG. 1, and generally indicated at 10, consists of a substrate of coated web paper stock having a paper sheet base 12 and a polymeric clay or kaolin coating 14. The coating provides a smooth impervious surface to which the applied layer can lightly adhere, and from which it can readily be removed. A layer of fragrance oil microcapsules 18 is applied to the smooth coated surface 14 of the paper stock in a liquid slurry, the liquid being a volatizing agent which rapidly evaporates on drying, leaving a solid readily removable powder layer.

The dry powdered layer on application of light finger pressure will break up into discrete powder particles light powder representative of the fragranced powder of which it is a sample.

Figure 2:
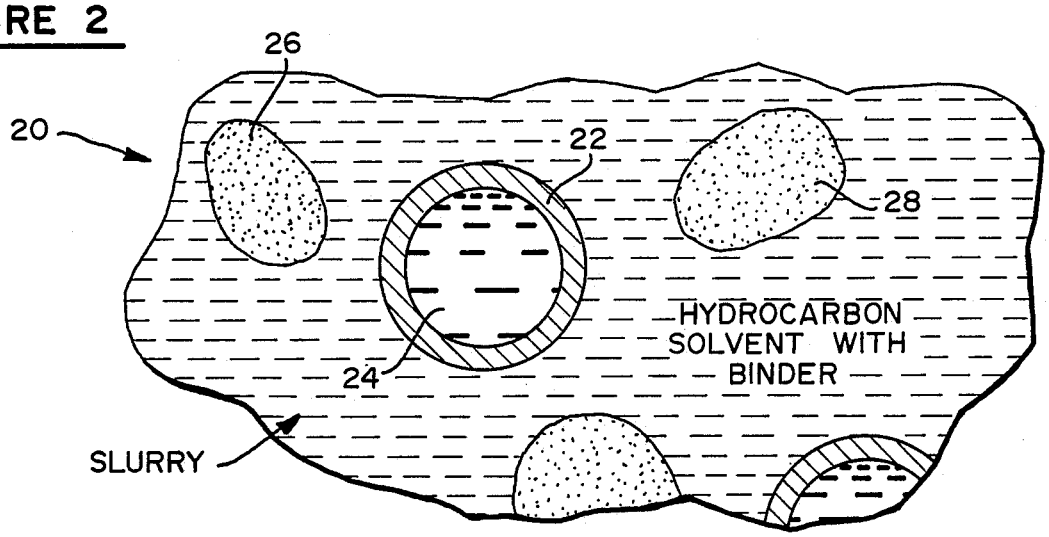
FIG. 2 is an enlarged view of a representative portion of the liquid slurry before application to the sampler.

The drawing of FIG. 2 shows a portion of the liquid slurry solution prior to its application to the web. The portion of the slurry generally indicated at 20, is a hydrocarbon solvent suspension containing powder particles and fragrance encapsulated microcapsules. The microcapsules have a gelatin wall 22 which encloses a fragrance oil 24. The powder particles of talc 26 and 28, are also shown. The hydrocarbon solvent is a isoparaphinic hydrocarbon which quickly volatizes. It is sold under the trade name of ISOPAR C by the Exxon Corporation.

The slurry has the following elements and percentages by weight:

| | |
|---|---|
| Hydrocarbon solvent | 45.15% |
| Mineral Oil | 1.00 |
| Methyl glucoside | 0.50 |
| Silica | 1.00 |
| Microcapsules | 12.00 |
| Powder | 40.00 |
| Polysiloxane | 0.25 |
| Preservative | 0.25 |
| Preservative | 0.10 |

The capsules are preferably in the 10 to 60 micron range, but it is possible to use microcapsules that have a size in the range of from 5 to 300 microns.

The powder is a talc or commercially formulated bath or body powder.

Figure 3:
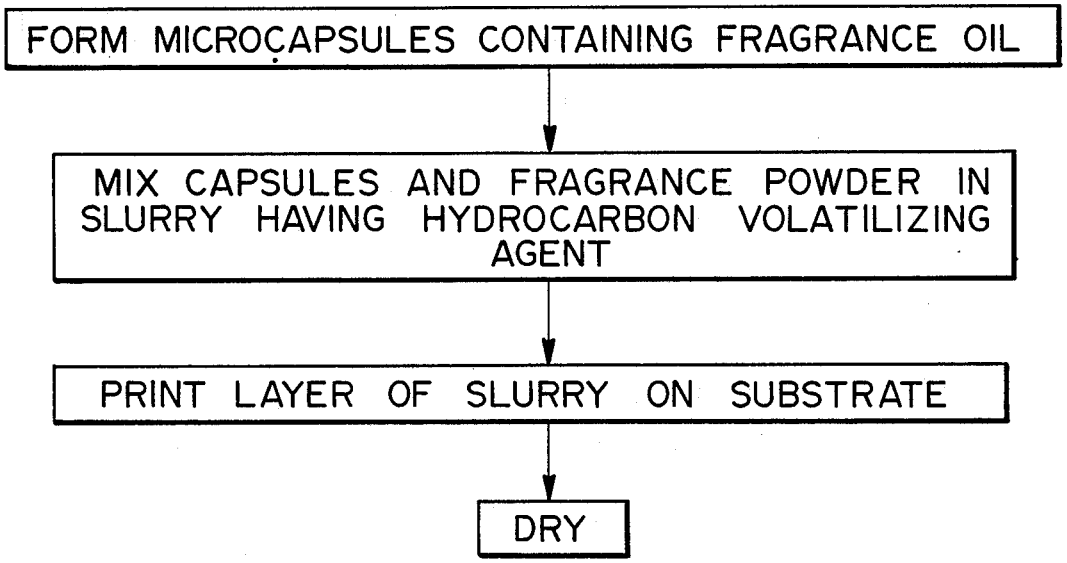
FIG. 3 shows the steps involved in applying the fragrance powder layer to the sampler of FIG. 1.

FIG. 3 shows the basic steps of the method employed in applying the powder layer 18 of FIG. 1. The fragrance oil is microencapsuled and the microcapsules are then dried. The slurry is then prepared by mixing the powder formulation constituents mentioned above and then mixing the dried capsules into the mixture.

The slurry is printed as a layer onto the coated paper stock of the web at one of the intermediate production stages in the continuous forming method of the sampler items from a roll of paper stock.

Figure 4:
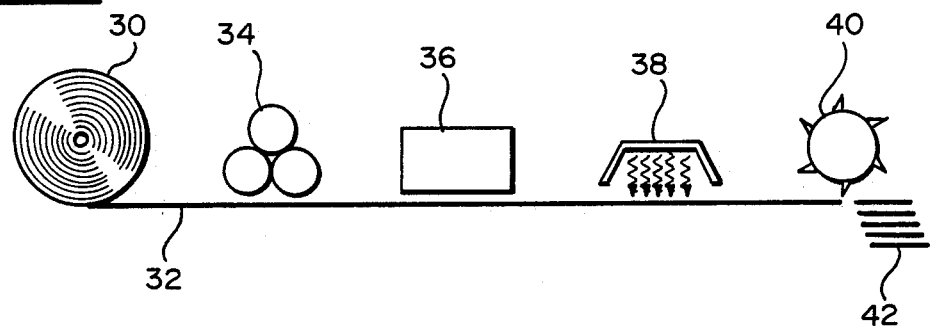
FIG. 4 is a schematic view of the web production process for the sampler of FIG. 1.

FIG. 4 shows schematically a simplified method of producing the sampler items. The roll of coated paper stock 30 supplies a web of paper 32 which passes through a printing stage 34. A strip of slurry material is applied at 36. The slurry can be applied by printing methods including gravure, flexography and screen printing techniques. It is also possible to extrude the powder and capsule layer onto the web, and to use wire wound rods.

A drying unit 38 applies heat to the passing web to evaporate the volatizing agent which leaves the dry powdery particle and capsule layer lightly adhered to the paper stock surface. The powder particles do not stick together, but are fragrancing when removed.

The cutter 40 cuts the web transversely to produce separate printed and coated blanks into a plurality of samples 42 containing printed matter referring to the sampler layer and the removable powder and fragrance capsule layer.

One of the important aspects of this method is the use of a hydrocarbon volatizing agent in the particle/microcapsule slurry. Alcohols, such as ethyl alcohol, while serving as a satisfactory volatizing agent in many cases, would not be acceptable in this instance. The gelatin wall of the microcapsules have been found to degrade and possibly rupture in an alcohol solution. Also, if there is a fragranced oil in the powder particles, there is a tendency for the alcohol to partially extract these oils. The isoparaphinic hydrocarbon used in the slurry, such as ISOPAR C, function similarly to the alcohols, but do not have the drawback of permeating the gelatin walls, or exchanging with the fragrance oil.

Figure 5:
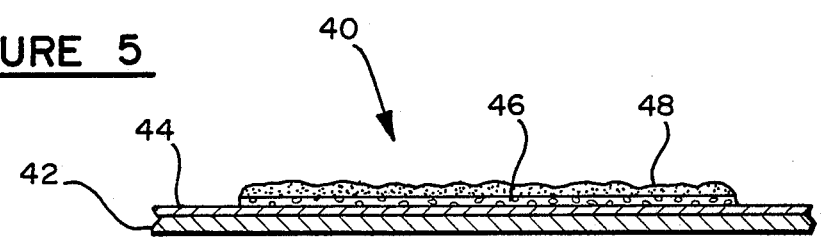
FIG. 5 is a cross-sectional view of a modification of powder layer sampler.

FIG. 5 shows a cross-section of another type of fragrance powder/microcapsule cosmetic sampler. The sampler section generally indicated at 40 has the coated paper stock with the paper material 42, covered by the clay coating 44. An underlayer 46 containing microcapsules is applied as a first layer. The upper covering layer 48 is the slurry composition of the first example without the microcapsules.

Figure 6:
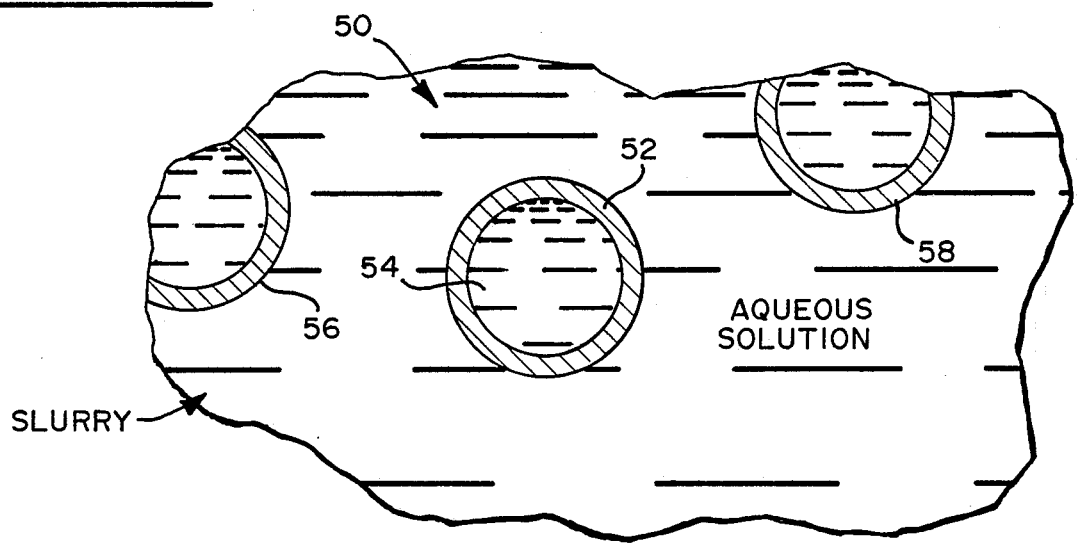
FIG. 6 shows a magnified view of a representative portion of the liquid slurry used to produce the fragrance layer of the sampler of FIG. 5.

FIG. 6 is an enlarged portion of the slurry mixture used for the underlayer 46. The slurry generally indicated at 50 contains a gelatin wall microcapsule having a gelatin wall 52 and the encapsulated fragrance oil 54. Similar microcapsules 56 and 58 are shown. The constituents of this slurry are those of the example given for the first modification, without the fragrance powder. The size of the capsules are preferably 10 to 60 microns, and the general range of 5 to 300 microns is similar to the capsule size of the first example.

FIG. 7 shows the basic steps of the two layer method of forming the sampler. Individual microcapsules containing fragrance oil are formed and dried. They are then mixed in the slurry composition of FIG. 6. The slurry is then applied to the smooth coating 44 of the coated stock, and then dried. The fragrance powder layer slurry, previously mixed, is then applied on top of the dried capsule layer and itself subsequently dried.

FIG. 8 shows a simplified schematic of the method used to produce samplers from a continuous web. The web of coated paper stock 62 is unwound from the paper roll 60. It passes through printing stages generally indicated at 64 which print successive sampler blanks on the web. The under layer application stage 66, which is applied by printing or extrusion techniques, is applied to the designated section of the sampler blank as a wet slurry layer. The web then passes under the drying stage, such as an infrared drying section which dries the layer 46 of microcapsules.

The slurry containing the fragrance particles is then applied to stage 76 over the under layer 46 and subsequently dried at stage 78 leaving the dried residual layer of fragrance particles 48.

The successive blanks containing the two layers of particles, are severed from the web by cutter 80 to produce a plurality of separate cosmetic sampler pieces 82.

The fragranced powder layer consists of a suspended lose mixture of fragranced powders such as talc or of commercially available fragrance powder particles. The upper surface 18 of the layer is relatively uniform. The powder layer is dry to the touch and on light contact pressure, will come off the paper as a plurality of discrete, free-flowing particles of dry powder. The consistency and color, as well as the scent will closely match an advertised commercial product which it represents. Both the powder consistency and the fragrance are closely matched.

It is also important that the fragrance of the particles when the sample layer is removed from the sampler surface of the same strength as that of a freshly opened package or container. In this respect, the sealing in of the fragrance is necessary to preclude loss of fragrance during handling and distribution of the samples. Prolonged shelf life is an important consideration.

The fragrance particles shown can either be ordinary talc, or a commercially available fragrance powder. Commercially available powder has approximately a 10 to 15% fragrance oil content which would be supplemented by an additional 10% by weight addition of fragrance oil. Unfragranced talc particles would have up to 25% by weight of fragranced oil added to the talc particle.

The particles are mixed with binders and a volatizing agent to produce a slurry liquid which is readily printable or extruded onto paper.

A typical formulation of ingredients with the relative ranges for the type of elements is as follows for the general category of elements that make up the composition:

| | |
|---|---|
| (a) the volatizing agent | 44 to 84% by weight; |
| (b) adhesion/cohesion promoters and rheological agents | 0 to 6% by weight; |
| (c) fragrance oil | 6 to 7% by weight; (fragranced) up to 6 to 16% by weight (Unfragranced Particles) |
| (d) rheology and processing agents | 0 to 4% by weight; |
| (e) lubricants | 0.25 to 1.5% by weight; |
| (f) preservatives | .05 to .10% by weight; |
| (g) powders either fragranced or unfragranced | 15 to 50% by weight |

The solvents under (a) above include: Ethanol, isopropanol, methyl isobutyl ketone, hydrocarbon solvents, heptane, trichlorotri fluoroethane, etc.

A solvent suitable for formulation can vary according to the specific needs of a particular formulation goal or a solvent can be chosen by virtue of drying rate, flamability, or other such criteria if a specific formulation property is not required.

The adhesion/cohesion elements under (b) above include: Methyl glucoside, mineral oils, hexylene glycol, propylene glycol, cetyl palmitate and other fatty alcohols, etc.

This category is a combination of adhesion/cohesion promoters, color/texture enhancers, processing aids (rheological, suspension etc.) fragrance fixatives etc. Any of these and other suitable raw materials can be utilized to impart or enhance whatever specific qualities or characteristics are desired.

The fragrance oil ((c) above) is added to import a greater initial pre-odor to the sample. The oil is added with the adhesion/cohesion materials usually, but it could be withheld from the batch until the time of actual printing.

The agents under (d) above include: silica, zinc stearate, calcium stearate etc. The adhesion/cohesion materials of item (b) are often utilized in combination with these materials to aid in rheology control, improve processing (both printing and bulk manufacturing) and to promote finished product characteristics such as longevity of fragrance, and adhesion and cohesion of the powders.

Item (e) above includes: polysiloxane, cyclomethicone, dimethyl polysiloxane etc.

Materials in this category are preferably silicone based materials which aid in manufacturing and processing by internally lubricating the system aiding mixing, pumping and overall processing. *

The use of a preservative is optional.

The powders included under (g) above includes both fragranced and unfragranced powder.

Any material in a powder form can be processed by varying or modifying the formulation as necessary. This including but is not limited to bath powders, eye shadows, talcum powders etc.

The percentages that are given for the prepared example, is for the constituent percentages in the slurry or
*This material may be omitted however, the addition of one or more of these materials will aid overall processing. the liquid applied layer. On drying the vaporizing agent leaves the layer, and the percentages by weight of the dried layer will proportionately increase, reflecting the percentages loss of the volatizing agent, such as the ethyl alcohol in the example.

While this invention has been described as having preferred design, it is understood that it is capable of further modification, uses and/or adaptations of the invention following in general the principle of the invention and including such departures from the present disclosure as come within known or customary practice in the art to which the invention pertains, and as may be applied to the essential features set forth, and fall within the scope of the invention or the limits of the appended claims.

What is claimed is:

1. A particle and fragrance capsule sampler, comprising:
   (a) a substrate having a surface;
   (b) microencapsulated fragrance oil;
   (c) solid powder particles;
   (d) each of said powder particles being formed of homogeneous material;
   (e) said microencapsulated fragrance oil and said solid powder particles forming a layer on said surface of said substrate;
   (f) said microcapsules and said powder particles forming mixture;
   (g) said mixture also including a binding material;
   (h) said powder particles being held temporarily in fixed position with respect to each other by the set taken by the binding material; and
   (i) said powder particles and said binding material taking a set within the layer as a residual dried layer after evaporation of a volatile liquid suspension medium originally mixed with the layer, whereby the particles lightly adhere to the substrate surface, and on application of light finger pressure, virtually all of said powder particles are removable therefrom as discrete free-flowing separate particles, having the property of a fragranced powder, and the microcapsules break to release the fragrance oils resulting in the consistency and scent of a fragranced powder.

2. The particle and fragrance capsule as set forth in claim 1, wherein
   (a) the microcapsules are within the range of 5 to 300 microns in size.

3. The particle and fragrance capsule as set forth in claim 1, wherein:
   (a) the microcapsules are from 50 to 60 microns in size.

4. The particle and fragrance capsule sampler as set forth in claim 1, wherein:
   (a) the volatizing agent of the liquid suspension for the particles is only a small residual percentage thereof, such agent being a hydrocarbon solvent.

5. A particle and fragrance capsule sampler, comprising:
   (a) a substrate having a smooth surface,
   (b) an underlayer of microcapsules containing fragrance oil disposed on and lightly adherent to the smooth surface of the substrate,
   (c) a top layer of readily removable dry adhesively held particles disposed on the underlayer and adherent thereto,
   (d) the top layer also including a binding material,
   (e) the powder particles being held temporarily in fixed position with respect to each other by the set taken between the particles and the binder material,
   (f) the particles of the top layer and the microcapsules of the bottom layer intermixing with each other and the microcapsules breaking to free the fragrance oils upon application of light finger pressure, such that the particles assume a discrete free-flowing characteristic and the released scent of the fragrance oil resulting in a representation of the properties of a freshly opened package of fragranced powder.

6. The particle and fragrance capsule as set forth in claim 5, wherein:
   (a) the percentage by weight of the particles in the top layer is approximately 90% by weight, and approximately 100% binder by weight.

* * * * *